(12) United States Patent
Genovese et al.

(10) Patent No.: US 8,404,490 B1
(45) Date of Patent: Mar. 26, 2013

(54) DETECTING NERVE AGENTS AND DETERMINING THE TYPES THEREOF

(75) Inventors: James A. Genovese, Street, MD (US); Robin L. Matthews, Port Deposit, MD (US); Kwok Y. Ong, Joppa, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 67 days.

(21) Appl. No.: 13/295,669

(22) Filed: Nov. 14, 2011

Related U.S. Application Data

(62) Division of application No. 11/610,241, filed on Dec. 13, 2006, now Pat. No. 8,057,761.

(51) Int. Cl.
  *B01L 3/00* (2006.01)
  *G01N 33/00* (2006.01)
  *A62D 3/35* (2007.01)

(52) U.S. Cl. .......... 436/104; 422/558; 588/317
(58) Field of Classification Search .......... 422/558; 436/104; 588/317
See application file for complete search history.

(56) References Cited

U.S. PATENT DOCUMENTS

| | | | | |
|---|---|---|---|---|
| 4,816,414 A | * | 3/1989 | Koocher et al. | 436/85 |
| 5,035,860 A | * | 7/1991 | Kleingeld et al. | 422/413 |
| 6,228,657 B1 | * | 5/2001 | Genovese et al. | 436/167 |
| 6,420,181 B1 | * | 7/2002 | Novak | 436/104 |
| 2003/0153021 A1 | * | 8/2003 | Lu et al. | 435/7.32 |

* cited by examiner

*Primary Examiner* — Lore Jarrett
(74) *Attorney, Agent, or Firm* — Ulysses John Biffoni

(57) ABSTRACT

An embodiment of a chemical detector has at least one detection window and at least first and second ampoules selectively communicatively coupled to the at least one detection window. The first ampoule contains a first substance that can hydrolyze a nerve agent. The second ampoule contains a second substance that can react with a hydrolyzed nerve agent to produce a color change.

12 Claims, 9 Drawing Sheets

$$CH_3 - \overset{\overset{O}{\|}}{\underset{\underset{O}{|}}{P}} - F$$

- Fluoride leaving group
- Methyl Group
- Ether linkage
- iPr

Sarin (GB)

FIG. 7

DETECTING NERVE AGENTS AND DETERMINING THE TYPES THEREOF

RELATED APPLICATIONS

This application is a divisional of application Ser. No. 11/610,241 filed Dec. 13, 2006, which issued as U.S. Pat. No. 8,057,761 on Nov. 15, 2011.

GOVERNMENT INTEREST

The invention described herein may be manufactured, licensed, and used by or for the U.S. Government.

TECHNICAL FIELD

The present invention relates generally to chemical detection and in particular the present invention relates to detecting nerve agents and determining the types thereof.

BACKGROUND

Chemical warfare agents, such as the nerve agents GB and VX, pose a toxic and persistent hazard to conventional military forces and possibly to civilian populations. These chemical warfare agents are potentially employed as a tactical or terror weapon in various military scenarios, such as being deployed in military actions for effective terrain denial, using a variety of dissemination mechanisms including grenades, mortars, mines, rockets, bombs, long-range projectiles, and missiles.

A chemical agent detector has been developed for detecting a variety of chemical warfare agent vapors or gases, e.g., non-persistent nerve vapors, blood gases, and liquid blister agents. An example of a chemical agent detector for detecting a variety of chemical warfare agent vapors or gases is an M256A1 Chemical Agent Detector Kit. A chemical agent detector for detecting solid, liquid, or vapor chemical hazards has also been developed. An example of such a detector is an M256 LVHD (Low Volatility Hazard Detector), which is a standard M256A1 Chemical Agent Detector, modified to include low volatility liquid and solid sampling and detection. In particular, the M256 LVHD includes a sample heater assembly that can be used with an M256A1 Chemical Agent Detector to effectively vaporize one or more low volatility agents for detection thereof. The M256A1 and the M256 LVHD are described in Department of the Army Technical Manual, TM 3-6665-307-10, titled An Operators Manual for Chemical Agent Detector Kit, M256 (6665-01-016-8399) and M256A1 (6665-01-133-4964), September 1985, the entire contents of which are incorporated herein by reference. One problem with these detectors is they cannot distinguish between classes within the nerve agent family, e.g., between G-type nerve agents and V-type nerve agents.

SUMMARY

An embodiment of a chemical detector has at least one detection window and at least first and second ampoules selectively communicatively coupled to the at least one detection window. The first ampoule contains a first substance that can hydrolyze a nerve agent. The second ampoule contains a second substance that can react with a hydrolyzed nerve agent to produce a color change.

BRIEF DESCRIPTION OF THE DRAWINGS

FIG. 7 illustrates the molecular structure of a G-type nerve agent.

DETAILED DESCRIPTION

In the following detailed description of the present embodiments, reference is made to the accompanying drawings that form a part hereof, and in which are shown by way of illustration specific embodiments that may be practiced. These embodiments are described in sufficient detail to enable those skilled in the art to practice disclosed subject matter, and it is to be understood that other embodiments may be utilized and that process changes may be made without departing from the scope of the claimed subject matter. The following detailed description is, therefore, not to be taken in a limiting sense, and the scope of the claimed subject matter is defined only by the appended claims and equivalents thereof.

Figure 1:
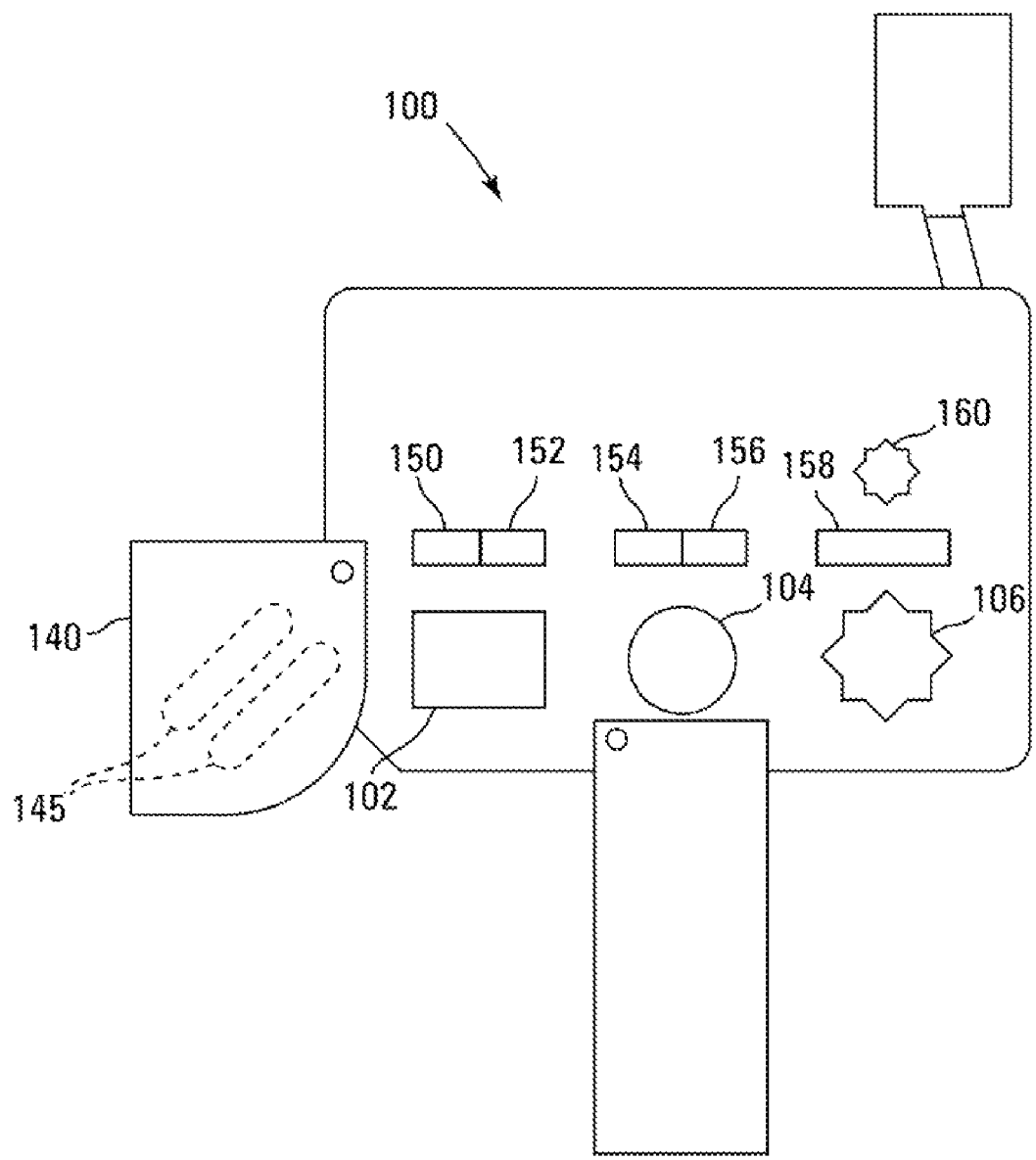
FIG. 1 is a back view of a detector of the prior art.

FIG. 1 is a back view of a detector 100 of the prior art, such as the M256A1 Chemical Agent Detector, that can analyze chemical vapors and gasses. Detector 100 includes a square-shaped detection window 102, a circular-shaped detection window 104, and a star-shaped detection window 106, the backsides of which are shown in FIG. 1. Detection window 102 is used in the detection of blister agents, such as a liquid mustard agent (e.g., HD mustard), detection window 104 in the detection of a blood gas such as hydrogen cyanide, and detection window 106 in the detection of nerve agents (e.g., VX or GB Sarin).

Figure 3:
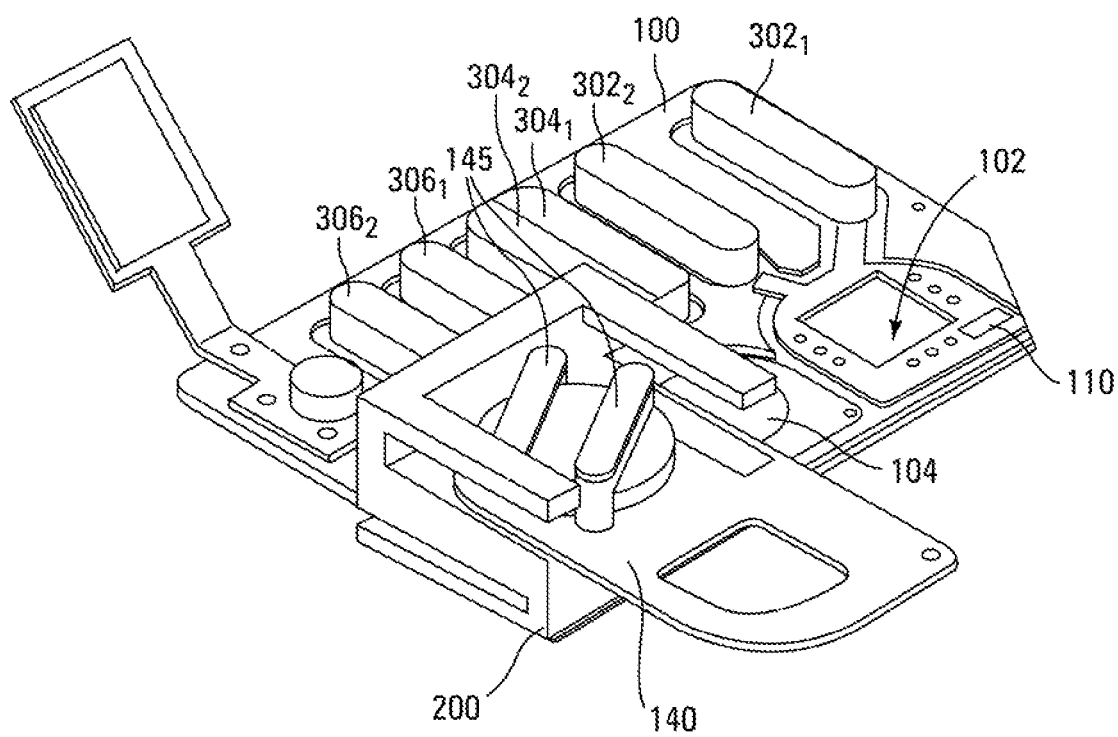
FIG. 3 is a front view of the detector of FIG. 1 including the sample heater assembly of FIG. 2.

Detector 100 includes ampoules 302, 304, and 306 that are respectively selectively communicatively coupled to detection windows 102, 104, and 106, as shown in FIG. 3, a front view of detector 100. Ampoules 302, 304, and 306 contain reagents are released into their respective detection windows 102, 104, and 106 when the ampoules are crushed. The reagents of ampoules 302, 304, and 306 respectively produce color changes (or colorimetric reactions) in detection windows 102, 104, and 106 in the presence of particular hazardous chemical vapors or gases.

Figure 2:
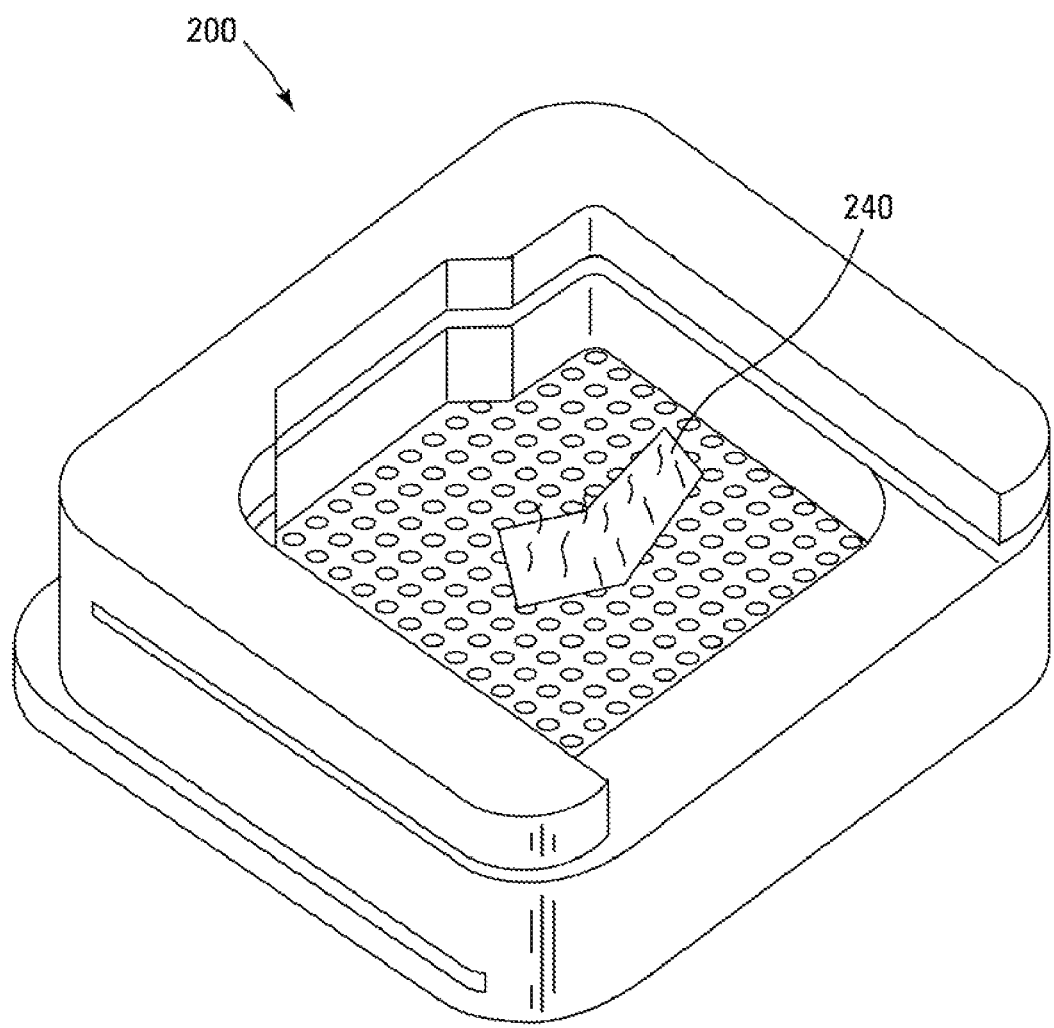
FIG. 2 illustrates a sample heater assembly of the prior art.

Detector 100 may include a heating element 140, as shown in FIG. 3, that includes two glass reactant vials 145 that when broken give off heat. FIG. 2 illustrates a sample heater assembly 200 of the prior art. Sample heater assembly 200 and heating element 140 are used in combination with detector 100, as shown in FIG. 3, to increase the effective vapor pressure of low volatility hazardous liquids or solids, particularly nerve agents, such as VX. An example of a detector 100 combined with sample heater assembly 200 and heating element 140 is an M256 Low Volatility Hazard Detector (M256 LVHD), as described in application U.S. patent application Ser. No. 10/633,733, filed Aug. 4, 2003 and issued as U.S. Pat. No. 7,036,388 on May 2, 2006, the entire contents of which are incorporated herein by reference.

Sample heater assembly 200 is positioned over one of the detection windows 102, 104, or 106, such as detection window 106, as shown in FIG. 3. A chemical detection paper 240 (e.g., M8 Liquid Agent Detection Paper or M9 paper), containing a sample, e.g., a hazardous liquid absorbed by the paper or a solid attached to the paper, is disposed in heater assembly 200, as shown in FIG. 2. Heating element 140 is inserted into sample heater assembly 200, as shown in FIG. 3, so as to cover chemical detection paper 240 containing the sample. Glass vials 145 of heating element are crushed, producing heat that vaporizes the liquid sample contained by chemical detection paper 240. Liquid reagents are then released into the detection window with the heater assembly 200 positioned thereover, e.g., window 106 in FIG. 3, by crushing the corresponding ampoules, e.g., ampoules 306. The reagents produce a color change (or colorimetric reaction) in the corresponding window when a hazardous chemical is present.

The reagents contained in the ampoules in detector 100 are selected to produce a color in a corresponding detection window that matches the color of color comparator located above the corresponding the detection window. A purple-blue color comparator 150 and a red-purple color comparator 152 are located above detection window 102, as shown in FIG. 1, and correspond to the color of detection window 102 in the presence of blister agents, e.g., respectively of mustard (H or HD) and phosgene oxime (CX). No color change in detection window 102 in response to the reagent indicates that there is no blister agent present, e.g., no hazard. A pink color comparator 154 and a blue color comparator 156 are located above detection window 104 (FIG. 1) and correspond to the color of detection window 104 in the presence of blood agent. No color change or a color change to tan indicates no hazard. A white color comparator 158 is located above detection window 106 (FIG. 1) and corresponds to the color of detection window 106 in the presence a nerve agent. A blue-green color comparator 160 is located above detection window 106 and corresponds to the color of detection window 106 when there is no hazard.

Note that detector 100 (e.g., configured as an M256A1 Chemical Agent Detector) can be used to detect hazardous vapors or gases, such as blister agents, blood, and nerve agents, directly by releasing reagents into a window exposed to a vapor or gas and by comparing the resulting color of the window to a comparator located above the window. Detector 100 (e.g., configured as an M256 LVHD Chemical Agent Detector) can also be used to detect hazardous liquids or solids, such as blister agents, blood, and nerve agents, by vaporizing a liquid or solid so as to expose a preselected window to the vapor, releasing reagents into an exposed window, and comparing the resulting color of the window to a comparator located above the window. However, detector 100 cannot provide a tactical confirmation as to what class of nerve agents is detected when the color of window 106 is white, indicating the presence of a nerve agent. That is, detector 100 cannot be used to determine whether the detected nerve agent is a volatile G-type nerve agent or a non-volatile V-type nerve agent. The only fielded systems that can distinguish G-type nerve agents from V-type nerve agents are presumptive liquid agent detectors, such as M8 Liquid Detection papers. The alternative is the very sophisticated and limited quantity mass spectrometric systems found in NBC (Nuclear, Biological, and Chemical) Reconnaissance Vehicles.

Figure 4:
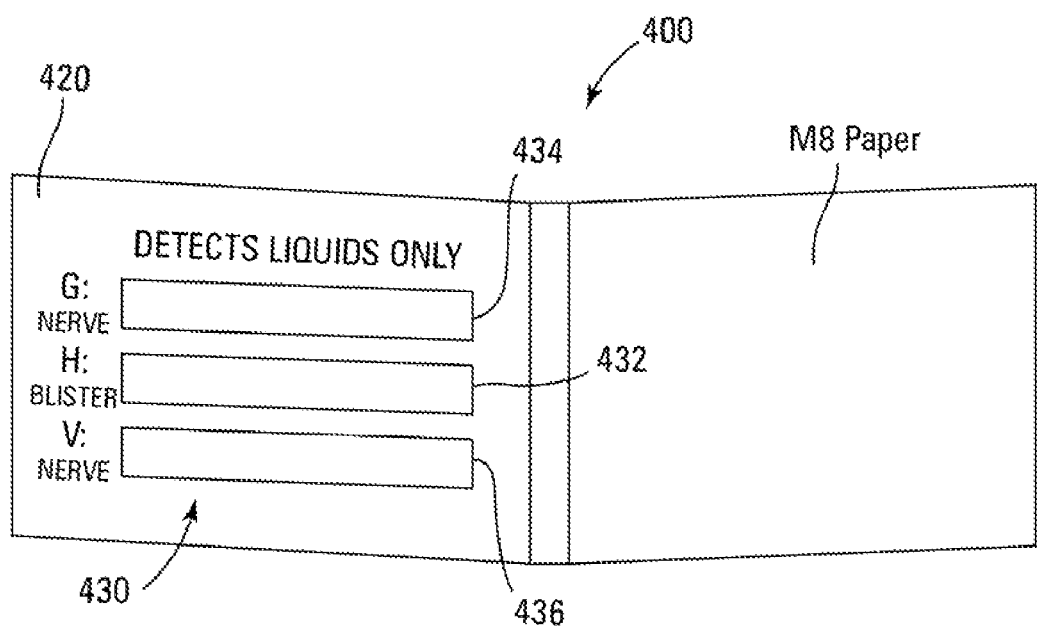
FIG. 4 is an illustration of a booklet of M8 Liquid Agent Detection Paper.

M8 Liquid Agent Detection Paper is employed in the M256 LVHD, but it still does not adequately discriminate the possible nerve agents being detected, such as liquid G-type nerve agent or liquid V-type nerve agent. M8 Liquid Agent Detection Paper is dipped into a suspect liquid and absorbs that liquid. Any resulting color change in the M8 paper is compared to the colors of color comparators of an M8 color key 430 (shown in FIG. 4) disposed on a backside 420 of the cover of a booklet 400 of M8 paper. A color match indicates the possible presence of an agent hazard. For example, if the M8 paper turns red, it matches color comparator 432 of color key 430, indicating the possible presence of a liquid blister agent. If the M8 paper turns yellow or gold, it matches color comparator 434 of color key 430, indicating the possible presence of a liquid G-type nerve agent. If the M8 paper turns green, it matches color comparator 436 of color key 430, indicating the possible presence of a liquid V-type nerve agent. For some V-type nerve agents, the M8 paper first turns green and then turns from green to brown. Although the M8 paper does provide some colorimetric discrimination of G-type nerve agents from V-type nerve agents, M8 paper uses simple acid-base principles for discrimination that are prone to false positive reactions from environmental interferents. Therefore, M8 paper does not provide a full proof discrimination method. M8 Chemical Agent Detection Paper is described in army Supply Bulletin SB 3-6665-2, the entire contents of which are incorporated herein by reference.

Detector 100 configured for analyzing liquids or solids, e.g., configured as the M256 LVHD, is used, as described above, to determine whether the liquid sample absorbed by the M8 Paper (when the paper turns color) is a hazard or a false positive. That is, sample heater assembly 200 is positioned over a detection window of detector 100 associated with the potential hazard, as shown in FIG. 3; the sample-containing M8 paper is disposed in the sample heater assembly 200, as shown in FIG. 2, and is vaporized into the detection window; and vaporized sample reacts with the reagents that are released into the detection window from the ampoules, as described above. If the color from the M256 detection window indicates a hazard, the liquid sample is a hazard.

Specifically, for a nerve agent, the color of the M8 paper indicates the possible presence of a G-type nerve agent by turning yellow or gold or a V-type nerve agent by turning green or by turning green and then brown. The sample heater assembly 200 is positioned over starred detection window 106, for nerve agents, of detector 100, as shown in FIG. 3. The liquid absorbed in the yellow or gold or green or brown M8 paper is vaporized in sample heater assembly 200, thereby exposing detection window 106 to the vapor. If the reagent released from ampoules 306 causes detection window 106 to turn white, the liquid is a G-type nerve agent when the M8 paper is yellow or gold and a V-type nerve agent when the MS paper is green or brown. If the window 106 turns blue-green, this indicates that no nerve agent hazard is present, and therefore, the liquid which turned the M8 Paper either gold or green was an organic liquid that happened to react with one of those dyes impregnated in the M8 Paper. In this case the M8 color detection is considered a false positive.

M9 paper contains a single dye and turns red when dipped into a liquid nerve agent (either a G-type nerve agent or a V-type nerve agent) or when dipped into a blister agent and exhibits no color change when dipped into a liquid that does not contain a liquid nerve agent or a liquid blister agent. Similar, to M8 paper, M9 paper is susceptible to interferents and thus some organic liquids can cause a change in M9 paper, thus indicating a false positive. Therefore, M9 paper indicates the possibility of a liquid nerve agent or a liquid blister agent when it turns red.

As described above in conjunction with the M8 paper, detector 100 configured for analyzing liquids or solids, e.g., configured as the M256 LVHD, can be used to determine whether the liquid sample contained in the M9 paper is a hazard or a false positive. That is, the liquid contained in the M9 paper can be vaporized in the sample heater assembly 200 while the sample heater assembly 200 is located over the starred detection window 106, thereby exposing detection window 106 to the vapor. If the reagents released from ampoules 306 causes detection window 106 to turn white, the liquid is either a G-type nerve agent or a V-type nerve agent when the M9 paper is red. If the detection window 106 turns blue-green, this indicates that no nerve agent hazard is present, and therefore, the liquid which turned the M9 Paper red was an organic that happened to react with the dye impregnated in the M9 Paper. In this case the M9 color detection is considered a false positive or possibly a blister agent. In that case one may want to insert the sample heater assembly of FIG. 2 over the detection window 102 for detecting blister agents, as shown in FIG. 1. Therefore, using M9 paper in conjunction with detector 100 configured for analyzing liquids or solids cannot differentiate between the types of liquid nerve agents, nor can it distinguish nerve from blister agents.

The liquid sample absorbed in the M9 paper can also be vaporized in sample heater assembly 200 while sample heater assembly 200 is located over square detection window 102, thereby exposing detection window 102 to the vapor. If the reagents released from ampoules 302 (FIG. 3) causes detection window 102 to turn a purple-blue color, a liquid mustard blister agent is present when the M9 paper is red or causes detection window 102 to turn a red-purple color liquid when phosgene oxime blister agent is present when the M9 paper is red. No color change in window 102 indicates, firstly, that no blister agent is present, and so when the M9 paper is red, this indicates a false positive for blister agent caused by an interfering organic liquid or possibly the presence of a liquid nerve agent.

Figure 5:
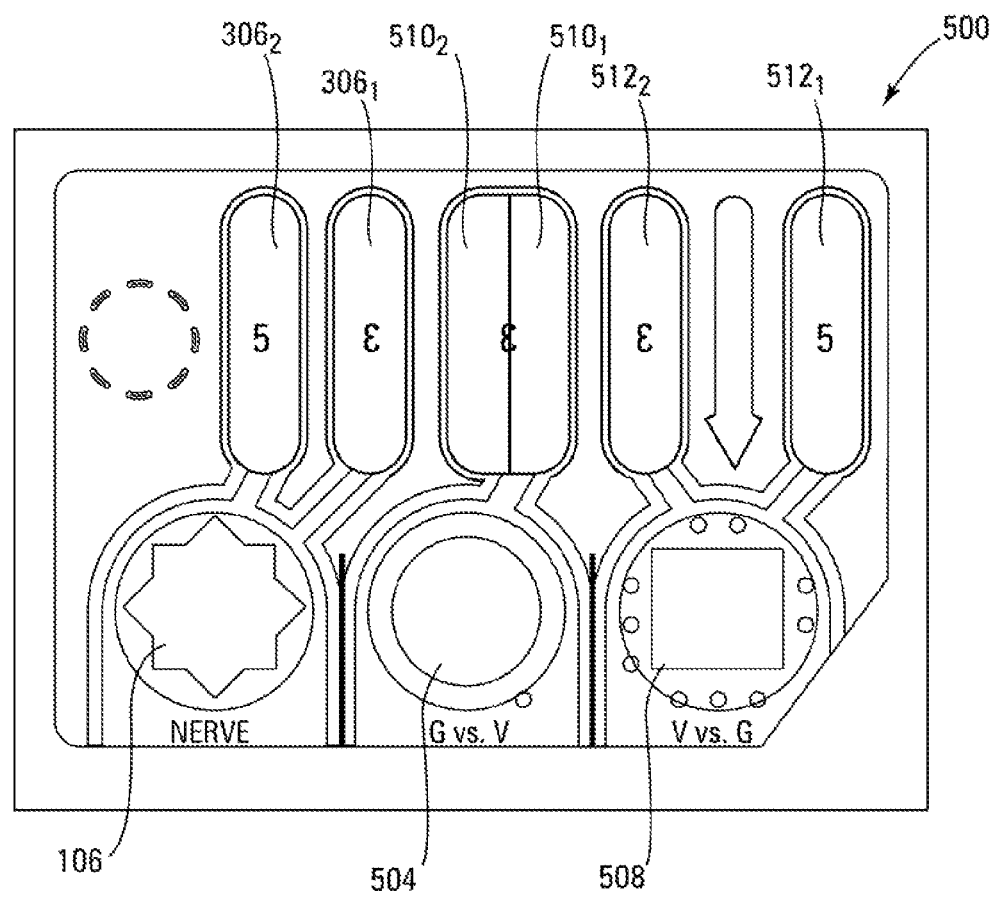
FIG. 5 is a front view of an embodiment of a detector, according to an embodiment of the disclosure.
Figure 6:
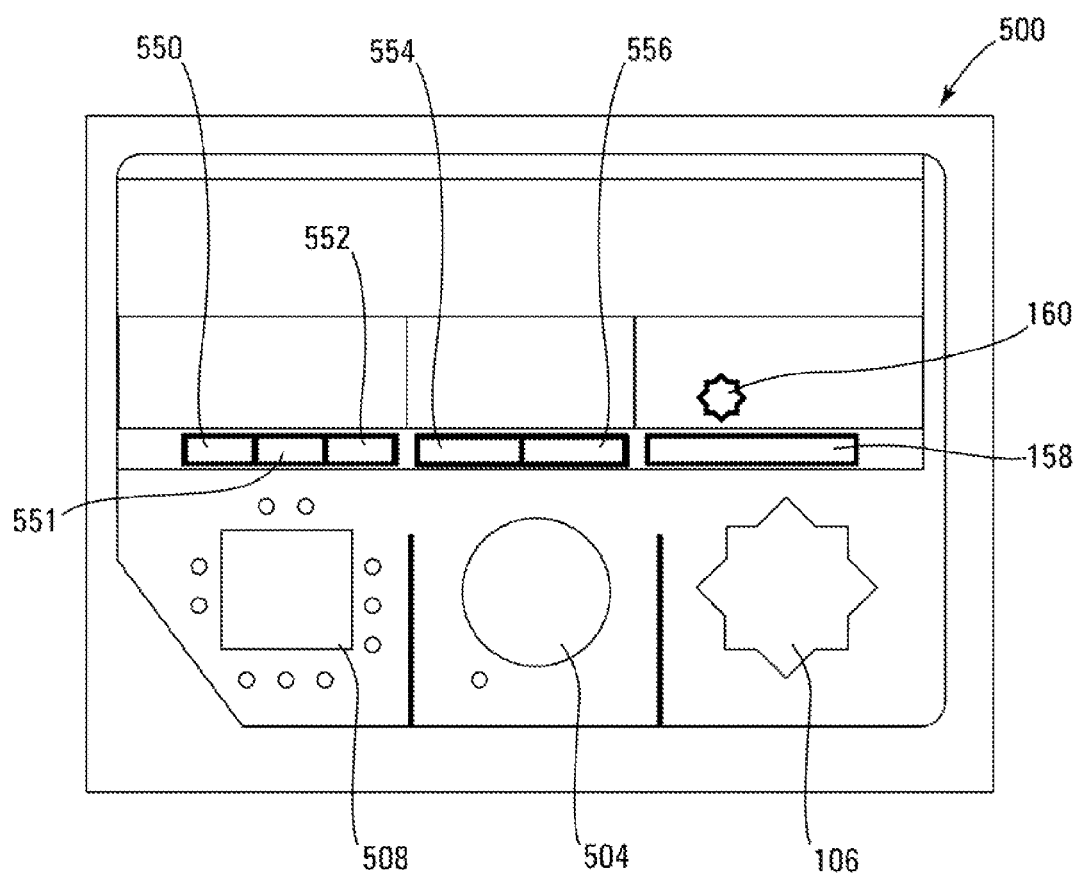
FIG. 6 is a back view of an embodiment of a detector, according to another embodiment of the disclosure.

FIG. 5 is a front view of a detector 500, according to an embodiment. FIG. 6 is a back view of detector 500, according to another embodiment. For one embodiment, detector 500 is configured to detect and discriminate between gaseous or vaporous G-type and V-type nerve agents. For another embodiment, detector 500 is configured to detect and discriminate between liquid G-type and V-type nerve agents and thus includes a sample heater assembly, such as the sample heater assembly 200 described above in conjunction with FIGS. 2 and 3, and a heating element, such as the heating element 140 described above in conjunction with FIGS. 2 and 3. For another embodiment, detector 500 is configured to detect and discriminate between liquid G-type and V-type nerve agent that can be manually deposited directly on to the detector 500 detection windows possibly using a pipetting method. For another embodiment, detector 500 may be a modified M1256A1 Chemical Agent Detector for analyzing gasses and vapors or a modified M256 LVHD Chemical Agent Detector for analyzing liquids and solids, e.g., vaporizing the liquids and solids and subsequently analyzing the resulting vapors. For one embodiment, detector 500 is an adjunct to detector 100 of FIGS. 1-3, e.g., detector 500 is an adjunct to the M256A1 Chemical Agent Detector or the M256 LVHD Chemical Agent Detector.

Detector 500 includes the star-shaped detection window 106 and the ampoules 306 of detector 100. Star-shaped detection window 106 and ampoules 306 are operated as described above in conjunction with detector 100 for determining whether a sample is a nerve agent. Note that for one embodiment, sample heater assembly 200 and element 140 are positioned over detection window 106, as shown in FIG. 3 and described above, for vaporizing a liquid or solid sample. Note that the white color comparator 158 is located above the backside of detection window 106, and the blue-green color comparator 160 is also located above the backside of detection window 106, as shown in FIG. 6. Note further that releasing reagents from ampoules $306_1$ and $306_2$ into detection window 106 when a nerve agent is present in detection window 106 causes detection window 106 to turn white, as described above in conjunction with detector 100. If no nerve agent is present, window 106 turns blue-green when reagents from ampoules $306_1$ and $306_2$ are released into detection window 106. For one embodiment, ampoule $306_1$ contains 2,6-dichloroindophenyl acetate and ligroine, and ampoule $306_2$ contains a buffer (e.g., pH of about 8), such as tris-(hydroxymethyl)-amino-methane, hydrochloric acid, and aerosol OT.

Detector 500 also includes a circular-shaped detection window 504 selectively communicatively coupled to ampoules $510_1$ and $510_2$. For one embodiment, detection window 504 and ampoules $510_1$ and $510_2$ are respectively modifications of detection window 104 and ampoules $304_1$ and $304_2$ of detector 100 (FIG. 3). That is, the chemistry of the contents of ampoules $510_1$ and $510_2$ of detector 100 have been changed for determining whether a nerve agent is a G-type nerve agent or a V-type nerve agent. For one embodiment, no color change (or colorimetric reaction) occurs in detection window 504 when reagents from ampoules $510_1$ and $510_2$ are released into detection window 504 when a G-type nerve agent is present in detection window 106, whereas at least a portion of detection window 504 turns dark (e.g., brown) when reagents from ampoules $510_1$ and $510_2$ are released into detection window 504 when a V-type nerve agent is present in detection window 504.

A dark-colored, e.g., brown, color comparator 554 is located above the backside of detection window 504, as shown in FIG. 6, and corresponds to the color of window 504 in the presence of a V-type nerve agent. A clear white comparator 556 is also located above the backside of detection window 504, as shown in FIG. 6, and corresponds to the color of window 504 in the presence a G-type nerve agent. Note that brown comparator 554 and clear white comparator 556 are respectively modifications of the pink color comparator 154 and blue color comparator 156 of detector 100 (FIG. 1).

Identification of a G-type nerve agent or V-type nerve agent in detection window 504 involves hydrolyzing the sample in detection window 504, e.g., using a base hydrolysis with a pH greater than about 9, and subsequently treating the hydrolyzed sample to cause a "leaving group" of the hydrolyzed sample to undergo reaction, such as a ionic reaction. For one embodiment, the "leaving group" undergoes a precipitation reaction and produces a precipitate when a V-type nerve agent is present in detection window 504, causing detection window 504 to turn dark. When a G-type nerve agent is present, the reaction of the hydrolyzed sample does not produce a substantially observable precipitation, and no color change occurs in detection window 504.

Figure 8:
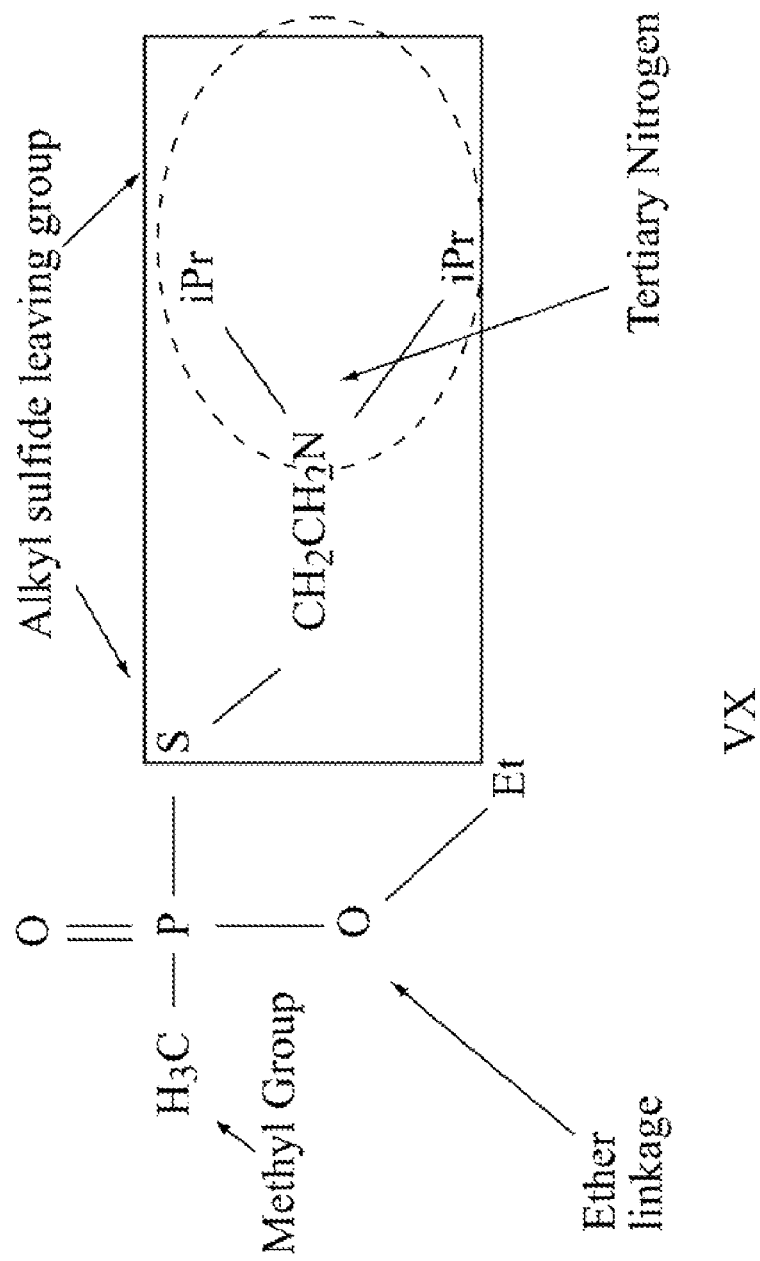
FIG. 8 illustrates the molecular structure of a V-type nerve agent.

FIGS. 7 and 8 respectively illustrate examples of the molecular structure of a G-type nerve agent, such as isopropyl methylphosphonofluoride, i.e., Sarin (or GB), and a V-type nerve agent, such as O-ethyl S-(2-diisopropylamino) ethyl methylphosphonothioate, i.e., VX. Note that GB and VX both are pentavalent organophosphorus compounds. That is, both the GB and VX molecules have five bonds to a central phosphorus atom and doubly-bonded oxygen that is also bonded to the central phosphorus atom. Both the GB and VX molecules have an ether linkage (P—O—R) to the central phosphorus atom. GB has a isopropyl ether linkage, whereas VX has an ethyl ether linkage. Both molecules have a methyl group attached to the left of the central phosphorus atom, as presented.

FIG. 7 shows that the most notable functional group of the GB molecule is a lone fluorine atom attached directly to the central phosphorus atom. This occurs for almost all of the G-type nerve agents. For almost all of the V-type nerve agents, the most noticeable functional group is a long chain alkyl sulfide, as shown for VX in FIG. 8. The two different groups on the right hand-side of the central phosphorus atom, as presented are called "leaving groups" when GB or VX undergo a chemical reaction called hydrolysis. Hydrolysis is a specific chemical reaction that many organic molecules undergo when they react directly with water and is pH dependent. In this hydrolysis, water serves as the nucleophile in a base catalyzed attack on the electropositive phosphorous atom. To effectively detect and discriminate the G-type nerve agents from the V-type nerve agents, these distinctive functional groups of the V-type nerve agents and G-type nerve agents are targeted.

GB and VX can undergo hydrolysis or hydrolyze in either acidic or basic environments. When base hydrolysis (e.g., for pH greater than about 9) occurs with GB, the fluorine atom (the leaving group) leaves as the unprotonated fluoride ion. When VX undergoes base hydrolysis, the large alkyl sulfide to the right of the central phosphorus atom is the leaving group that separates from the molecule.

After the GB is hydrolyzed, the following ionic reaction takes place when the fluoride leaving group is treated with a Silver Nitrate solution (e.g., having a concentration of approximately 0.1M $AgNO_3$), for example:

$$F^- + Ag^+ \rightarrow AgF$$

That is, the fluoride leaving group reacts with the silver ion from the silver nitrate solution and forms a soluble, clear solution with substantially no observable precipitation.

After the VX is hydrolyzed, the following ionic reaction takes place when the fluoride leaving group is treated with a Silver Nitrate solution (e.g., having a concentration of approximately 0.1 M $AgNO_3$), for example:

$$S-R^- + Ag^+ \rightarrow AgSR \downarrow$$

That is, the large alkyl sulfide leaving group reacts with the silver ion in the silver nitrate to produce a substantially insoluble, dark precipitate, indicative of silver-sulfide chemistry. Note that conventional chemistry uses shorthand notation like "R" to indicate alkyl functional groups, such as $-CH_3$ and $-CH_2CH_3$.

The combination of the base hydrolysis of an unknown nerve agent, followed by a silver nitrate reaction can identify and discriminate nerve agents that have fluoride leaving groups from those nerve agents that have alkyl sulfide leaving groups. Substantially all G-type nerve agents will have the fluoride leaving group and will not generate a precipitate. Substantially all V-type nerve agents will have the alkylsulfide leaving group and a dark precipitate will be formed. Note that the base hydrolysis reaction of the unknown nerve agent and the subsequent silver nitrate reaction occur in detection window 504.

For one embodiment, detection window 504 includes a filter-type substrate, such as Whatman #1 paper. Ampoule $510_1$ contains a hydrolyzing reagent (or buffer), such as an alkaline solution or other suitable basic nucleophile, e.g., 1N $NaHCO_3$ with a pH of about 8 or above, to drive the base catalyzed hydrolysis of a sample contained in the filter-type substrate. Ampoule $510_2$ contains a reagent for reacting with the leaving group of the hydrolyzed sample, such as a silver nitrate solution, e.g., 0.1N $AgNO_3$. Note that because silver nitrate is photosensitive the 500 detection ticket is stored in an opaque aluminum foil pouch.

In operation, the filter-type substrate of detection window 504 is exposed to a sample; the alkaline solution is released from ampoule $510_1$ and onto the filter-type substrate for hydrolyzing the sample; the silver nitrate solution is released from ampoule $510_2$ and onto the filter-type substrate; and the leaving group of the hydrolyzed sample reacts with the silver nitrate solution. Note that the leaving group undergoes a precipitation reaction and produces a precipitate when a V-type nerve agent is present in detection window 504, causing detection window 504 to turn dark. Substantially no observable precipitation occurs when a G-type nerve agent is present in detection window 504 and a soluble, clear solution is produced that does not cause detection window 504 to change color.

For one embodiment, the sample may be determined to be a nerve agent using detection window 106 and ampoules 306, as described above, before exposing detection window 504 to the sample and analyzing the sample using detection window 504. That is, by detection window 106 turning white. For another embodiment, detection window 504 may be exposed by vaporizing a liquid or solid sample using sample heater assembly 200 and heating element 140 disposed over detection window 504. One may also directly deposit potential nerve agent sample directly on the nerve detection window 106 using possibly a pipetting method.

Detector 500 also includes a square-shaped detection window 508 selectively communicatively coupled to ampoules $512_1$ and $512_2$, as shown in FIG. 5. For one embodiment, detection window 508 and ampoules $512_1$ and $512_2$ are respectively modifications of detection window 102 and ampoules $302_1$ and $302_2$ of detector 100 (FIG. 3). That is, chemistry of detection window 102 and the chemistry of the contents of ampoules $302_1$ and $302_2$ of detector 100 have been changed to further identify between G-type nerve agents or V-type nerve agents. For one embodiment, no color change (or colorimetric reaction) occurs in detection window 508 when reagents from ampoules $512_1$ and $512_2$ are released into detection window 508 when a G-type nerve agent is present in detection window 508, whereas at least a portion of detection window 508 changes color (e.g., to a rust color) when reagents from ampoules $512_1$ and $512_2$ are released into detection window 508 when a V-type nerve agent is present in detection window 508.

Colored color comparators 550 and 551 are located above the backside of detection window 508, as shown in FIG. 6. For one embodiment, color comparators 550 and 551 are respectively of a yellow-reddish color and a reddish-violet color and respectively correspond to the color of detection window 508 in the presence of two different types of V-type nerve agent. Note that the two color changes are both consistent with detection of tertiary amine compounds that are present in all V-type molecules. A clear comparator 552 is also located above the backside of detection window 504, as shown in FIG. 6, and corresponds to the color of window 508 in the presence a G-type nerve agent. Note that colored color comparator 550 and clear comparator 552 are respectively modifications of purple-blue color comparator 150 and red-purple color comparator 152 of detector 100 (FIG. 1).

Identification of a G-type nerve agent or V-type nerve agent in detection window 508 involves hydrolyzing the sample in detection window 508, e.g., using the alkaline buffer solution, e.g., 1N $NaHCO_3$, other buffer or hydrolyzing agents, described above in conjunction with detection window 504. The leaving group of the hydrolyzed sample is subsequently reacted with a polycarboxylic acid, such as a tricarboxylic acid, e.g., cis-aconitic acid, citric acid, isocitric acid, oxalic, malonic acid, etc., and an appropriate solvent, e.g., acidic anhydride, alcohol, other acetic-acid-based solvents, water, etc.

Note that the leaving group of the VX molecule in FIG. 8 has a tertiary nitrogen or tertiary amine in its structure. The polycarboxylic acid and the acidic anhydride react with the tertiary amine group of the VX molecule to produce a complex that has a rusty color. Note further that the leaving group of the GB molecule in FIG. 7 does not have a tertiary nitrogen or tertiary amine in its structure, but has just the lone fluorine atom that does not react with the polycarboxylic acid and acidic anhydride to produce a color change. Therefore, another method for identifying G-type and V-type nerve agents is provided.

For one embodiment, detection window 508 includes a filter-type substrate, such as Whatman #1 paper treated, e.g., impregnated, with polycarboxylic acid, e.g., cis-aconitic acid. For example, the cis-aconitic acid may be dissolved in water, e.g., 2 grams of cis-aconitic acid for every 100 milliliters of water, producing a cis-aconitic-acid-water solution. The cis-aconitic-acid-water solution, e.g., 50 milliliters, is then absorbed by the filter-type substrate, and the filter-type substrate containing the cis-aconitic-acid-water solution is subsequently air dried. Ampoule $512_1$ contains the buffer solution, e.g., 1N $NaHCO_3$. Ampoule $512_2$ contains the solvent, e.g., acidic anhydride.

In operation, the filter-type substrate of detection window 508, treated with a polycarboxylic acid, is exposed to a sample; the buffer solution is released from ampoule $512_1$ and onto the treated filter-type substrate for hydrolyzing the sample; and the solvent is released from ampoule $512_2$ and onto the filter-type substrate containing the hydrolyzed sample. When a V-type nerve agent is present in detection window 508, the tertiary amine of the leaving group of the hydrolyzed sample (FIG. 8) reacts with the polycarboxylic acid and the solvent from ampoule $512_2$, producing a color change (e.g., a yellow-reddish color or a reddish-violet color) in detection window 508. When a G-type nerve agent is present in detection window 508 there is no tertiary amine to react with the polycarboxylic acid and the solvent from ampoule $512_2$. Instead, there is the lone fluorine atom (FIG. 7) that does not react with the polycarboxylic acid and solvent to produce a color change, and no color change occurs in detection window 504. For one embodiment, after the solvent is released from ampoule $512_2$ and onto the filter-type substrate containing the hydrolyzed sample, the filter-type substrate containing the hydrolyzed sample and the solvent may be heated, e.g., using sample heater assembly 200 and heating element 140 (FIGS. 2 and 3) disposed over detection window 508. The heating acts to intensify the color change in the presence of V-type nerve agent for some embodiments.

For one embodiment, the sample may be determined to be a nerve agent using detection window 106 and ampoules 306, as described above, before exposing detection window 508 to the sample and analyzing the sample using detection window 508. That is, by detection window 106 turning white. For another embodiment, detection window 504 may be exposed by vaporizing a liquid or solid sample using sample heater assembly 200 and heating element 140 disposed over detection window 504. Detection window 504 can also be exposed by directly depositing the solid or liquid sample on to that detection window using a pipetting method.

For other embodiments, polycarboxylic acid, e.g., a 2 grams/100 milliliters cis-aconitic-acid-water solution, may be contained in a third ampoule (not shown) that is selectively communicatively coupled to detection window 508 rather than being impregnated in the filter-type substrate of detection window 508. As such, the filter-type substrate does not contain any reagent. For these embodiments, the plain filter-type substrate is exposed to a nerve agent; the buffer solution is released from ampoule $512_1$ and onto the filter-type substrate containing the nerve agent for hydrolyzing the nerve agent; the polycarboxylic acid is then added to the hydrolyzed nerve agent from the third ampoule; and the solvent is released from ampoule $512_2$ and onto the filter-type substrate containing the hydrolyzed nerve agent and the polycarboxylic acid. If the nerve agent is a V-type nerve agent, detection window 508 exhibits a colorimetric reaction or turns a color, such as reddish-violet or a red-yellowish hue. If the nerve agent is a G-type nerve agent, no color change occurs.

For one embodiment, first numerals, e.g., fives, may be embossed on ampoules $306_2$ and $512_1$, of detector 500, and second numerals may be embossed on ampoules $306_1$, $510_1$/$510_2$, and $512_2$, e.g., threes, of detector 500, as shown in FIG. 5, where the first and second numerals are rotated by 180 degrees with respect to each other. During operation, for another embodiment, of detector 500, reagent is released from the ampoules with the first numerals when the first numerals are right side up and the second numerals are upside down, and detector 500 is rotated by 180 degrees before reagent is released from the ampoules with the second numerals so that the reagent can be released from the ampoules with the second numerals when the second numerals are right side up and the first numerals are upside down.

Figure 9:
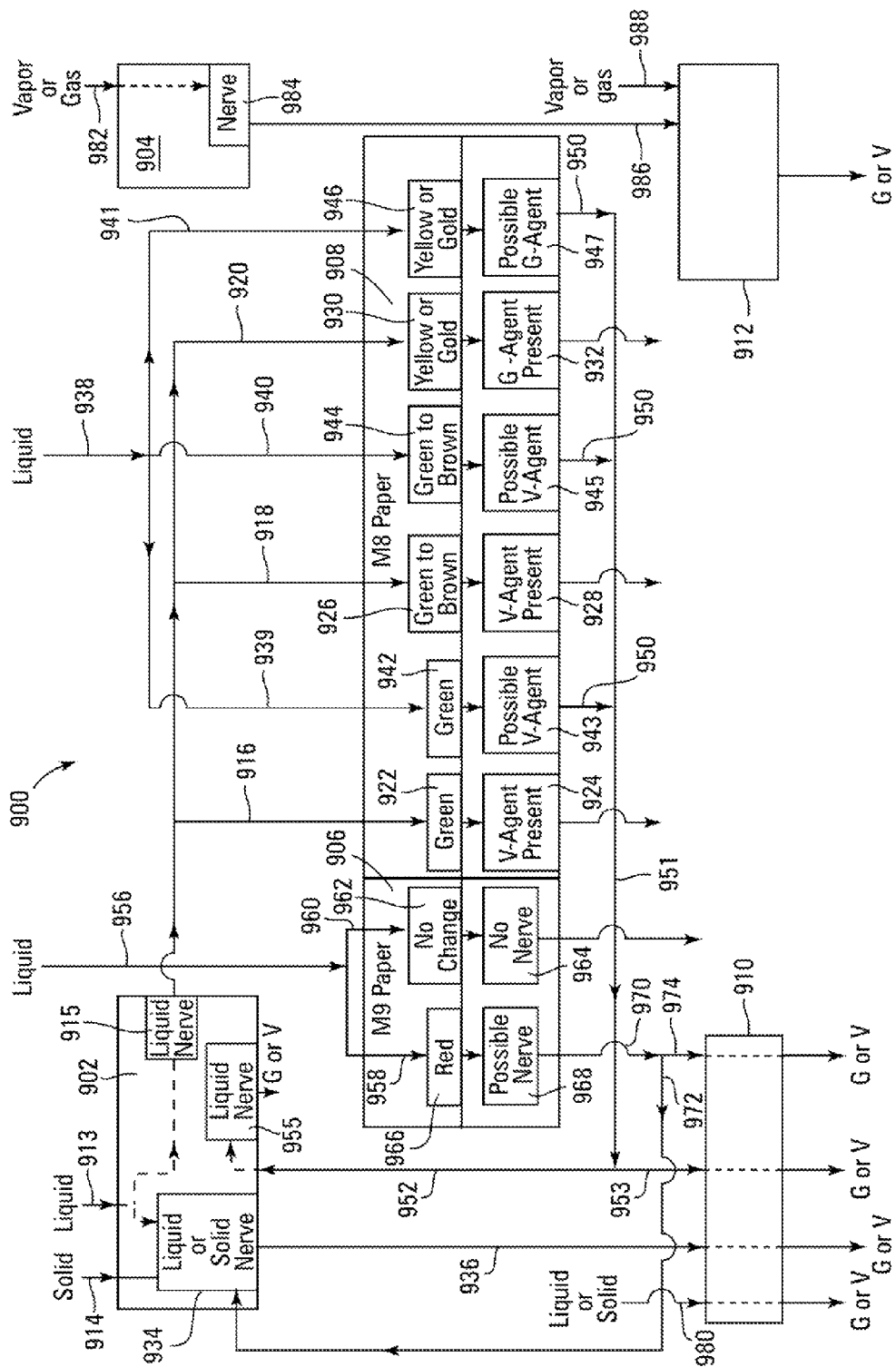
FIG. 9 is a block diagram of an embodiment a nerve agent detection/identification system, according to an embodiment of the disclosure.

FIG. 9 is a block diagram of a nerve agent detection/identification system (or kit) 900, according to an embodiment. The block diagram shows components of nerve agent detection/identification system 900, interactions between the components, and results or outputs of the components.

Nerve agent detection/identification system 900 includes a detector 902 that is configured for analyzing liquids, solids, or vapors. For one embodiment, detector 902 is similar to detector 100 of FIGS. 1-3, and includes a starred detection window, such as starred detection window 106 of detector 100, and reagent ampoules corresponding to the starred detection window, such as reagent ampoules 306 of detector 100, for nerve agents, a circular detection window, such as circular detection window 104 of detector 100, and reagent ampoules corresponding to the circular detection window, such as reagent ampoules 304 of detector 100, for blood, a square detection window, such as square detection window 102 of detector 100, and reagent ampoules corresponding to the square detection window, such as reagent ampoules 302 of detector 100, for blister agents, and a sample heater assembly and heating element, such as sample heater assembly 200 and heating element 140 of detector 100, for vaporizing liquids and solids For another embodiment, detector 902 may be a M256 LVHD Chemical Agent Detector.

Nerve agent detection/identification system 900 also includes a detector 904 configured for analyzing vapors and gasses, such as an M256A1 Chemical Agent Detector. Detector 904 includes, for one embodiment, a starred detection window, such as starred detection window 106 of detector 100, and reagent ampoules corresponding to the starred detection window, such as reagent ampoules 306 of detector 100, for nerve agents, a circular detection window, such as circular detection window 104 of detector 100, and reagent ampoules corresponding to the circular detection window, such as reagent ampoules 304 of detector 100, for blood, and a square detection window, such as square detection window 102 of detector 100, and reagent ampoules corresponding to the square detection window, such as reagent ampoules 302 of detector 100, for blister agents. Nerve agent detection/identification system 900 also includes liquid chemical detection paper 906, e.g., M9 paper, and liquid chemical detection paper 908, e.g., M8 paper.

Nerve agent detection/identification system 900 includes a detector 910, such as detector 500 of FIGS. 5 and 6 configured for analyzing liquid or solid nerve agents. For example, for one embodiment, detector 910 includes a starred detection window, such as starred detection window 106 of detector 500, and reagent ampoules corresponding to the starred detection window, such as reagent ampoules 306 of detector 500, for determining whether a nerve agent is present, a circular detection window, such as circular detection window 504, and reagent ampoules corresponding to the circular detection window, such as reagent ampoules 510 of detector 500, for determining the nerve agent type, a square detection window, such as square detection window 508 of detector 500, and reagent ampoules corresponding to the square detection window, such as reagent ampoules 512 of detector 500, for determining the nerve agent type, and a sample heater assembly and heating element, such as sample heater assembly 200 and heating element 140 of detector 100 (FIGS. 2 and 3), for vaporizing liquids and solids. Also directly depositing the sample on to these detection windows can also be performed for example with a pipet.

Detector 912 is also included for analyzing gaseous and vaporous nerve agents, e.g., detector 500 of FIGS. 5 and 6 without a sample heater assembly and heating element. For example, for one embodiment, detector 912 includes a starred detection window, such as starred detection window 106 of detector 500, and reagent ampoules corresponding to the starred detection window, such as reagent ampoules 306 of detector 500, for determining whether a nerve agent is present, a circular detection window, such as circular detection window 504 of detector 500, and reagent ampoules corresponding to the circular detection window, such as reagent ampoules 510 of detector 500, for determining the nerve agent type, and a square detection window, such as square detection window 508 of detector 500, and reagent ampoules corresponding to the square detection window, such as reagent ampoules 512 of detector 500, for determining the nerve agent type.

In operation, for a suspected liquid or solid nerve agent, the liquid or solid can be analyzed by detector 902, for one embodiment, as indicated by arrow 913 for liquids and arrow 914 for solids in FIG. 9. That is, the suspected liquid or solid nerve agent is vaporized into the starred detection window of detector 902, and if the starred detection window is white after the reagents are released from the ampoules corresponding to the starred detection window into the starred detection window, a nerve agent is present. If it is determined that a liquid nerve agent is present using detector 902, as indicated by block 915, the type of liquid nerve agent can be determined using M8 paper, as indicated by arrows 916, 918, and 920 of FIG. 9. That is, if the M8 paper turns green, as indicated by block 922, a V-type nerve agent is present, as indicated by block 924; if the M8 paper turns from green to brown, as indicated by block 926, a V-type nerve agent is present, as indicated by block 928; or if the M8 paper turns yellow or gold, as indicated by block 930, a G-type nerve agent is present, as indicated by block 932. If it is determined that a liquid or solid nerve agent is present using detector 902, as indicated by block 934, the type of liquid or solid nerve agent can be determined using detector 910, as indicated by arrow 936, by using the sample heater assembly and heating element of detector 910 with the circular detection window of detector 910 and reagents from the ampoules corresponding to the circular detection window and/or with the square detection window of detector 910 and reagents from the ampoules corresponding to the square detection window, as described above in conjunction with FIGS. 5-8.

For another embodiment, the M8 paper may be exposed to a suspected liquid nerve agent before using detector 902 or detector 910, as indicated by arrows 938, 939, 940, and 941. If the M8 paper turns green, as indicated by block 942, a possible V-type nerve agent is present, as indicated by block 943; if the M8 paper turns from green to brown, as indicated by block 944, a possible V-type nerve agent is present, as indicated by block 945; if the M8 paper turns yellow or gold, as indicated by block 946, a possible G-type nerve agent is present, as indicated by block 947.

After determining the possibility of a either a liquid V-type nerve agent or a liquid G-type nerve agent using the M8 paper, the starred window of detector 902 can be used, as indicated by arrows 950, 951, and 952, to determine whether the color change of the M8 paper is a false positive or is indicative of a nerve agent. Alternatively, the starred window of detector 910 can be used, as indicated by arrows 950, 951, and 953, to determine whether the color change of the M8 paper is a false positive or is indicative of a nerve agent. That is, the liquid is vaporized from the M8 paper into the starred window of detector 902 or 910, and the reagents from the ampoules corresponding to the starred detection window are released into the starred window. If the starred window of detector 902 turns white, indicating a liquid nerve agent, as indicated by block 955, a liquid V-type nerve agent is present when the M8 paper is green or turns from green to brown, or a G-type nerve agent is present when the M8 paper is yellow or gold. Similarly, if the starred window of detector 910 turns white, a liquid V-type nerve agent is present when the M8 paper is green or turns from green to brown, or a G-type nerve agent is present when the M8 paper is yellow or gold.

The liquid can be vaporized from the M8 paper into the circular detection window and/or the square detection window of detector 910. When the reagents from the ampoules corresponding to the circular detection window are subsequently released into the circular detection window, the circular detection window will show no colorimetric reaction or color change when a G-type nerve agent is present. Moreover, when the reagents from the ampoules corresponding to the square detection window are subsequently released into the square window, the square window will show no colorimetric reaction or color change when a G-type nerve agent is present. Note that a G-type nerve agent is indicated when the starred window of detector 902 or 910 is white and the M8 paper is yellow or gold. Therefore, nerve agent detection/identification system 900 provides three independent methods for identifying a G-type nerve agent.

When the reagents from the ampoules corresponding to the circular detection window of detector 910 are subsequently released into the circular window, the circular window will turn dark (or brown) when a V-type nerve agent is present. Moreover, when the reagents from the ampoules corresponding to the square detection window of detector 910 are subsequently released into the square window, the square window will exhibit a colorimetric reaction or color change, e.g., by turning a rust color, violet, or a yellowish hue, when a V-type nerve agent is present. Note that a V-type nerve agent is indicated when the starred window of detector 902 or 910 is white and the M8 paper is green or turns from green to brown. Therefore, nerve agent detection/identification system 900 provides three independent methods for identifying a V-type nerve agent.

For another embodiment, the M9 paper 906 may be exposed to a suspected liquid nerve agent before using detector 902 or detector 910, as indicated by arrows 956, 958, and 960. If the M9 paper does not change color, as indicated by block 962, no nerve agent is present, as indicated by block 964. If the M9 paper turns red, as indicated by block 966, there is a possible nerve agent or blister present. This could be verified by placing the contaminated M9 in the sample heater assembly of detector 902, e.g., the M256 LVHD, and inserting the sample heater assembly over the square detection window for blister agents to verify if the M9 color change is due to a blister agent, as indicated by block 968.

After determining the possibility of a liquid nerve agent using the M9 paper, the starred window of detector 902 can be used, as indicated by arrows 970 and 972 to determine whether the color change of the M9 paper is indicative of a nerve agent. Alternatively, the starred detection window of detector 910 can be used, as indicated by arrows 970 and 974, to determine whether the color change of the M9 paper is indicative of a nerve agent. That is, the liquid is vaporized from the M9 paper into the starred detection window of detector 902 or 910, and the reagents from the ampoules corresponding to the starred detection window are released into the starred window. If the starred detection window of detector 902 turns white, indicating a liquid nerve agent, as indicated by block 934, a liquid nerve agent is present when the M9 paper is red, and the type of liquid nerve agent can be determined from detector 910, as indicated by arrow 936, by vaporizing the liquid nerve agent, e.g., from the M9 paper, into the circular detection window of detector 910 and releasing reagents from the reagent ampoules corresponding to the circular detection window into the circular detection window and/or by vaporizing the liquid nerve agent into the square detection window of detector 910 and releasing the reagents from the reagent ampoules corresponding to the square detection window into the square detection window, as described above in conjunction with FIGS. 5-8. Similarly, if the starred window of detector 910 turns white, a liquid nerve agent is present when the M9 paper is red, and the type of liquid nerve agent can be determined from detector 910 using circular detection window of detector 910 and the reagents from the ampoules corresponding to the circular detection window and/or the square detection window of detector 910 and the reagents from the ampoules corresponding to the square detection window.

For another embodiment, detector 910 can be used directly to analyze a suspect liquid nerve agent, as indicated by arrow 980. That is, the liquid is vaporized into the starred detection window of detector 910, and the reagents from the ampoules corresponding to the starred detection window are released into the starred detection window. If the starred detection window turns white, a liquid nerve agent is present, and the type of liquid nerve agent can be determined from detector 910 using circular detection window of detector 910 and the reagents from the ampoules corresponding to the circular detection window and/or the square detection window of detector 910 and the reagents from the ampoules corresponding to the square detection window, as described above in conjunction with FIGS. 5-8.

For another embodiment, a vapor or gas may be analyzed by detector 904, as indicated by arrow 982. That is, the starred detection window of detector 904 is exposed to the vapor or gas, and reagents from the ampoules are released into the starred detection window. If the starred detection window is white, a nerve agent is present, as indicated by block 984. The type of vaporous or gaseous nerve agent can then be determined by detector 912, as indicated by arrow 986. That is, the circular detection window of detector 912 is exposed to the vapor or gas, and reagents are released into the circular detection window from the reagent ampoules corresponding to the circular detection window, and/or the square detection window of detector 912 is exposed to the vapor or gas, and reagents are released into the square detection window from the reagent ampoules corresponding to the square detection window, as described above in conjunction with FIGS. 5-8.

Alternatively, a vapor or gas may be analyzed by detector 912 directly, as indicated by arrow 988. That is, the starred detection window of detector 912 is exposed to the vapor or gas and reagents from the ampoules corresponding to the square detection window are released into the starred detection window. If the starred detection window is white, a nerve agent is present, and the type of nerve agent is determined from the circular detection window of detector 912 and the reagents from the ampoules corresponding to the circular detection window and/or from the square detection window of detector 912 and the reagents from the ampoules corresponding to the square detection window, as described above in conjunction with FIGS. 5-8.

CONCLUSION

Although specific embodiments have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of determining a type of a nerve agent, comprising:
   exposing a detection window of a detector to a nerve agent;
   hydrolyzing the nerve agent in the detection window by adding a first substance into the detection window; and
   adding a second substance to said hydrolyzed nerve agent contained in the detection window;
   wherein adding said second substance to hydrolyzed nerve agent causes the detection window to change color when the nerve agent is a V-type nerve agent or does not produce a color change when the nerve agent is a G-type nerve agent.

2. The method of claim 1, wherein polycarboxylic acid is impregnated in the detection window.

3. The method of claim 1, further comprising adding polycarboxylic acid to hydrolyzed nerve agent contained in the detection window before adding the second substance into the detection window.

4. The method of claim 1, wherein hydrolyzing the nerve agent comprises base hydrolysis.

5. The method of claim 1, wherein exposing said detection window of the detector to a nerve agent comprises vaporizing the nerve agent from a liquid or a solid.

6. The method of claim 1, wherein said second substance comprises a $AgNO_3$ solution.

7. The method of claim 6, wherein said second substance comprises an about 0.1N $AgNO_3$ solution.

8. The method of claim 1, wherein said first substance is selected from the group consisting of an alkaline solution and a basic nucleophile.

9. The method of claim 8, wherein said first substance is an about 1N $NaHCO_3$ buffering solution.

10. A method of determining a type of a nerve agent, comprising:
 exposing a detection window of a detector to a nerve agent;
 hydrolyzing the nerve agent in the detection window by adding a first substance into the detection window; and
 adding a $AgNO_3$ solution to said hydrolyzed nerve agent contained in the detection window;
 wherein the $AgNO_3$ solution reacts with hydrolyzed nerve agent in the detection window to form a precipitate that causes the detection window to change color when the nerve agent is a V-type nerve agent, or the $AgNO_3$ solution reacts with hydrolyzed nerve agent in the detection window to form a clear solution that does not produce a color change in the detection window when the nerve agent is a G-type nerve agent.

11. A method of determining a type of a nerve agent, comprising:
 exposing a polycarboxylic-acid-treated detection window of a detector to a nerve agent
 hydrolyzing the nerve agent in the detection window by adding a first substance into the detection window; and
 adding a second substance to the hydrolyzed nerve agent contained in the detection window;
 wherein the second substance reacts with said hydrolyzed nerve agent and polycarboxylic acid in the detection window when the nerve agent is a V-type nerve agent and causes the detection window to change color when the nerve agent is a V-type nerve agent, or the second substance does not react with hydrolyzed nerve agent and polycarboxylic acid in the detection window when the nerve agent is a G-type nerve agent, and the detection window does not change color when the nerve agent is a G-type nerve agent.

12. The method of claim 11, wherein said second substance comprises a $AgNO_3$ solution.

* * * * *